United States Patent [19]

Vetecnik

[11] Patent Number: 4,800,370
[45] Date of Patent: Jan. 24, 1989

[54] WETNESS DETECTION SYSTEM

[75] Inventor: Ivan Vetecnik, Salt Lake City, Utah

[73] Assignee: I E Sensors, Inc., Salt Lake City, Utah

[21] Appl. No.: 784,936

[22] Filed: Oct. 7, 1985

[51] Int. Cl.[4] .............................................. G08B 23/00
[52] U.S. Cl. ................................... 340/573; 128/886; 340/604
[58] Field of Search .............. 340/573, 604, 539, 620; 128/138 A; 200/61.04, 61.05

[56] References Cited

U.S. PATENT DOCUMENTS

| | | | |
|---|---|---|---|
| 3,460,123 | 8/1969 | Bass | 128/138 A |
| 3,588,858 | 6/1971 | Demuth | 340/539 |
| 4,106,001 | 8/1978 | Mahoney | 340/573 |
| 4,205,671 | 6/1980 | Lassen | 340/573 |
| 4,347,501 | 8/1982 | Akerberg | 340/573 |
| 4,356,818 | 11/1982 | Malias et al. | 128/138 A |
| 4,418,712 | 12/1983 | Braley | 200/61.04 |
| 4,450,431 | 5/1984 | Hochstein | 340/539 X |
| 4,539,559 | 9/1985 | Kelly et al. | 340/573 |
| 4,549,169 | 10/1985 | Moura et al. | 340/573 |

OTHER PUBLICATIONS

Barr, Ronald E.; A Telemetry System for Recording Body Temperature of Large Numbers of Caged Rodents; (1972), Med. & Biol. Eng.; vol. 10, #5, pp. 677–684.

Primary Examiner—Joseph A. Orsino
Assistant Examiner—Jeffrey A. Hofsass
Attorney, Agent, or Firm—Thorpe, North & Western

[57] ABSTRACT

A wetness detection system for detecting dampness in diapers or other articles of clothing includes a detector/transmitter which is attachable to the diaper or clothing. The detector/transmitter produces and transmits a signal when no urine or other conductive matter is present in the diaper or clothing, and this signal is received by and retransmitted from a retransmitting station which may, for example, be located on the bed of the person wearing the diaper or clothing. The retransmitted signal is ultimately received at a central station for alerting an attendant when a wetness condition is detected. Since signals are transmitted when no urine is present, the absence of signals over some predetermined period of time indicates that wetness is present.

14 Claims, 1 Drawing Sheet

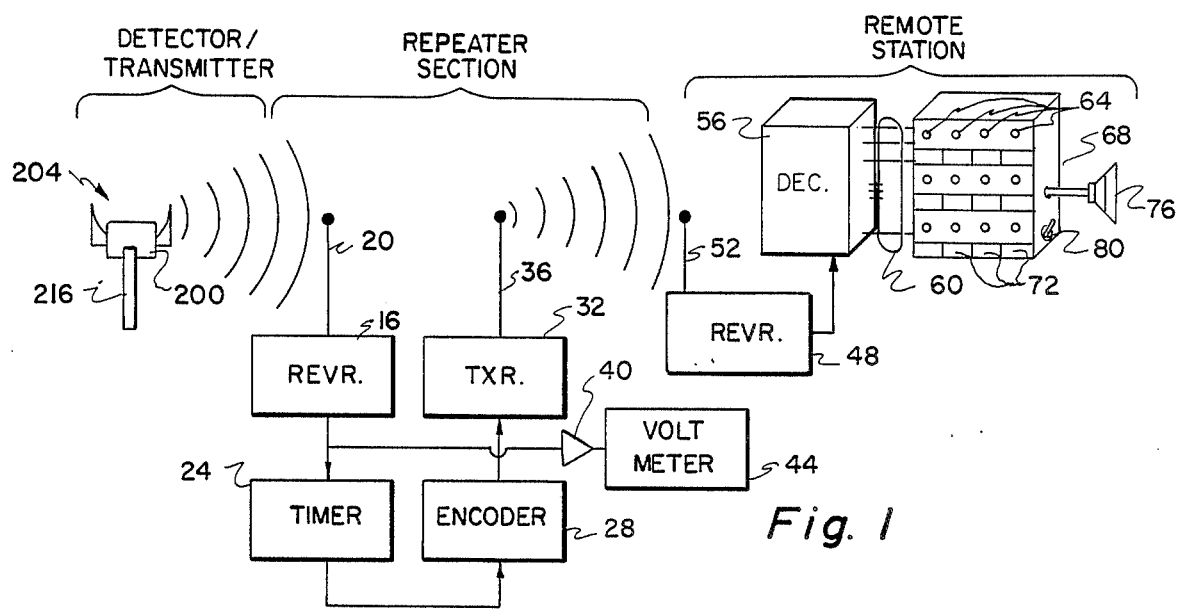
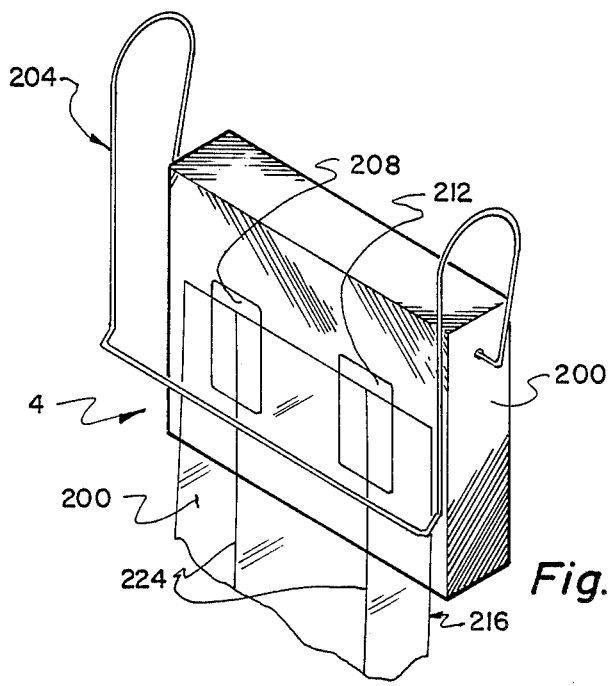
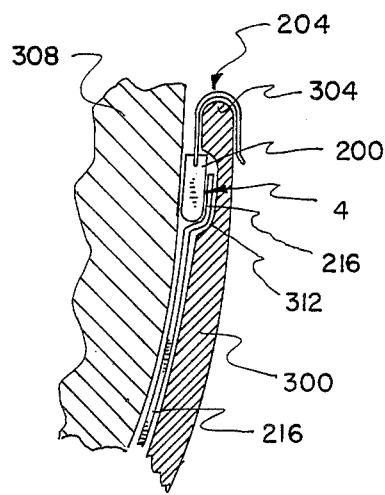
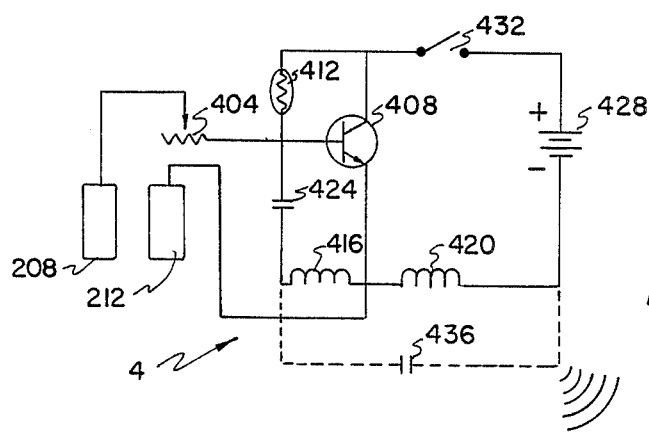

WETNESS DETECTION SYSTEM

BACKGROUND OF THE INVENTION

This invention relates to a system for detecting wetness in clothing and more particularly to a system for detecting the presence of urine in clothing worn by a infant or patient.

There are a variety of devices for sounding an alarm when an infant urinates in a diaper being worn by the infant. The reason for providing such alarm may be two-fold: (1) to alert the person caring for the infant that the diaper is wet and needs to be changed; and/or (2) to produce a startling or unpleasant event for the infant when the infant wets, hopefully leading to toilet training of the infant.

Devices such as described above have also been proposed for use on incontinent persons as well as infants to minimize the discomfort caused by the wearing of wet diapers or clothing. This objective, of course, can be achieved by promptly alerting those caring for the incontinent individuals or infants so that a change in the wet clothing can be made as promptly as possible. In addition to the discomfort of wearing wet clothing, rashes, skin irritations, and other adverse physical problems could develop.

Prior art devices for detecting dampness in clothing typically utilize electrodes positioned in the infant's diaper or mattress, with wire connections from the electrodes to an alarm mechanism mounted, for example, on the infant's bed. When urine or excrement provides an electrical connection between the electrodes, an audible or visual alarm is produced. An obvious drawback of this type of arrangement is that the wires connecting the electrodes to the alarm mechanism can interfere with movement of the infant and cause discomfort as well as pose a safety hazard. A number of devices have been proposed which would eliminate the need for wires but such devices typically are bulky, require installation in the fabric of the diaper and have a realtively short range and short life for the wireless transmitting equipment. Exemplary prior art devices are disclosed in U.S. Pat. Nos. 3,460,123, 3,508,235 and 4,205,672.

SUMMARY OF THE INVENTION

It is an object of the invention to provide a wetness detection system which is simple and yet effective in detecting urine in clothing and signalling an attendant.

It is another object of the invention to provide such a system which is relatively small in size and which may be readily installed and removed from a person's clothing.

It is further object of the invention to provide such a system which has a relatively long life and which does not require the use of connecting wires for producing alarm signals.

It is an additional object of the invention to provide a wetness detection system which, when put in place on an infant's clothing, produces relatively no discomfort.

The above and other objects of the invention are realized in a specific illustrative embodiment of a wetness detection system which includes a detector/transmitter which is attachable to a diaper or similar article of clothing for producing and transmitting a signal when no urine or other conductive matter is present in the diaper, a receiver for receiving the signal transmitted remotely by the detector/transmitter and for producing a receive signal in response thereto, a timer for producing a time-out signal if no receive signal is produced for some predetermined period of time, and a remotely located indicator or alarm for producing a visual or audible indication in response to the production of a time-out signal. In accordance with one aspect of the invention, a plurality of detector/transmitters, receivers and timers may be provided, each for a different patient. In such case, each timer would be associated with an encoder and transmitter which would encode a radio signal to identify an associated patient and transmit the signal to a remote station. The remote station would include a decoder for receiving transmitted radio signals, decoding the signals, and providing a visual identification of the patients designated by the transmitted radio signals. Then, an attendant at the remote station could simply observe the visual indications and immediately learn of infants whose diapers needed changing.

BRIEF DESCRIPTION OF THE DRAWINGS

The above and other objects, features and advantages of the invention will become apparent from a consideration of the following detailed description presented in connection with the accompanying drawings in which:

FIG. 1 is a block diagram and schematic of a wetness detection system made in accordance with the principles of the present invention;

FIG. 2 is a perspective, fragmented view of a detector/transmitter used in conjunction with the system of FIG. 1;

FIG. 3 is a side view of a detector/transmitter mounted on the inside of a diaper; and FIG. 4 shows a circuit schematic of a detector/transmitter suitable for use in the present invention.

DETAILED DESCRIPTION

Referring to FIG. 1 there is shown a wetness detection system which includes three sections--a detector/transmitter 4, is provided for attachment to the diaper or other article of clothing of an infant or incontinent person. The detector/transmitter 4 is provided for attachment to the diaper or other article of clothing of an infant or incontinent person. The detector/transmitter 4, which is shown in greater detail in perspective view in view in FIG. 2, includes a housing 200 having a generally flat or planar profile on which is mounted a spring clip 204. The housing 200 contains detector and transmitter circuitry, which will be described later, for detecting the presence of urine or other conductive matter in an article of clothing to which the housing is attached. Two electrodes 208 and 212 are exposed through a rear wall of the housing 200 to enable attachment thereto of an elongate conductor strip 216. The conductor strip 216, shown as being transparent in FIG. 2, comprises a strip of insulator material 220, such as acrylic tape made, for example, by Johnson & Johnson and sold under the name of "Dermiclear". The strip 216 has adhesive on a rear side for attachment to the back wall of the housing 200, and two elongate conductor wires carried on the opposite side of the strip generally in parallel with one another. The conductor wires 224, which advantageously would be made of copper or a copper alloy, could be held in place on the material 220 by a suitable adhesive.

The wire clip 204 is mounted on the housing 200 to extend outwardly from opposite sides thereof and then upwardly for a distance after which the clip loops downwardly to a location just above the bottom of the housing 200 and then inwardly to join as shown. With this arrangement, the detector/transmitter 4 may be clipped onto the upper edge 304 of a diaper 300 which has been placed on an infant or incontinent person 308. The housing 200 of the detector/transmitter 4 nestles in a depression 312 in the diaper 300 so that with the housing's generally planar profile there is little discomfort in attaching the detector/transmitter 4 inside the diaper. The conductor strip 216, as earlier described, is attached to the back of the housing 200 to extend downwardly under the housing and then downwardly between the skin of the person 308 and the diaper 216 as shown in FIG. 3. In this position, the conductor strip 216 and in particular the conductor wires 224 are in contact with a significant portion of the diaper so that when the diaper becomes wet, a conductive path may be established between the conductor wires.

As will be described in greater detail later, the detector/transmitter 4 is designed to continuously transmit a pulse signal train so long as there is no conductive path between the conductor wires 224. When a conductive path is established, then the detector/transmitter 4 ceases transmission of the pulse train. The advantage of continuous transmission with an interruption when urine is present in the diaper, rather than transmitting only when urine is detected, is that false signals or triggering of the transmitter can be avoided. This is done by simply timing over some period when transmission stops and then providing a suitable alarm signal if transmission does not begin again within that period. Obviously, if transmission is made only if wetness is detected, then a false signal or noise could give rise to a false alarm.

Referring again to FIG. 1, the repeater section 8 of the system is shown to include a receiver 16 having a receiving antenna 20. The receiver 16 receives the pulse train transmitted by the detector/transmitter 4 and supplies a reset pulse to a timer 24 with each pulse received from the detector/transmitter. If the receiver 16 receives no pulse signals from the detector/transmitter 4, then no reset signals are applied to the timer 24 which simply begins timing over some predetermined period. If the timer 24 "times out", it generates a signal which is supplied to an encoder 28. The encoder 28, in turn, supplies a coded signal identifying the detector/transmitter 4 with which it is associated, and supplies the signal to a transmitter 32 for transmission via an antenna 36 to the remote station 12. The transmitted signal contains information identifying the detector/transmitter 4 and thus the person on which the detector/transmitter is mounted.

The repeater section 8 would be located near the detector/transmitter 4, for example, such as on the bed of the patient wearing the detector/transmitter. For those patients who are ambulatory, the repeater section 8 could be worn by the patient. Of course, although not shown, the repeater section 8 would be carried in a housing with a strap or other attachment mechanism for mounting on the patient's bed or to enable the patient to "wear" the housing.

One other feature of the repeater section 8 involves apparatus for providing a reading of the patient's temperature. This apparatus includes a frequency-to-voltage convertor 40 and a voltmeter 44. The pulse train received by the receiver 16 from the detector/transmitter 4 is supplied to the convertor 40 which produces an output voltage whose magnitude is proportional to the frequency of the received pulses. This voltage signal is then supplied to a voltmeter 44 which produces a display of the voltage. As will be discussed inconnection with FIG. 4, the frequency of pulses transmitted by the detector/transmitter 4 are proportional to the temperature of the patient and therefore provide a measure of the patient's temperature. The reading of the voltmeter 44 thus provides an indication of the temperature of the patient. The remote station 12 is located centrally of the beds of the patients in order to receive transmitted radio signals from each of the repeater sections 8. The remote station 12 includes a receiver 48 with antenna 52 for receiving the encoded radio signals transmitted by the various repeater sections 8. The receiver 48 supplies the received signals to a decoder 56 which decodes each of the received signals and energizes one of lines 60 corresponding to the received signal. Each of the lines 60 is connected to a respective one of the lamps 64 mounted in a station console 68. Each lamp 64 is associated with a different one of the patients and is located above a corresponding name plate area 72 which would contain the name of the patient associated with the lamp. That is, when a particular patient's detector/transmitter 4 ceases transmitting, thereby indicating that the patient's diaper is wet, the identity of the patient would be encoded and transmitted by the repeater section 8, decoded at the remote station 12, and that patient's lamp lighted to signal an attendant that the patient needs changing.

Energization of any of the leads 60 also causes production and broadcasting of an audible signal by a speaker 76. Thus, any time an encoded radio signal is received at the remote station 12, one of the lamps 64 corresponding to the patient identified by the signal is lighted, and an audible signal is produced by the speaker 76 to warn the attendant.

The receiver 48 and decoder 56 are conventional devices. The station console 68 simply contains flip-flops for each of the lamps 64 which are set when a corresponding one of the leads 60 is energized to thereby supply power to light the lamps. A manual switch 80 is provided on the console 68 to reset the flip-flops after the diapers or wet clothing which caused the lighting of the lamps, are changed.

In the manner described, a single attendant can quickly examine the station console 68 to determine those patients whose lamps are lighted, and immediate action can be taken to change the diapers or wet clothing of those patients. The patients are subject to substantially no discomfort in the wearing of the detector/transmitter 4 and the detector/transmitter and repeater section 8 (which are associated with a single patient) are simple and yet efficient and accurate in detecting a wet or damp condition in the patient's clothing.

FIG. 4 shows a circuit schematic of the detector/transmitter 4. The circuit includes the two electrodes 208 and 212, the first of which is coupled via a variable resistor 404 to the base of a transistor 408. The other electrode 212 is coupled to the emitter of the transistor 408. A thermistor 412 interconnects the base and collector of the transistor 408. The emitter of the transistor 408 is also connected to a coil/antenna consisting of inductors 416 and 420. The inductor 416 is coupled in series with a capacitor 424 between the base and emitter electrodes of the transistor. The inductor 420 is coupled to one side of a battery 428, the other side of which is coupled via a switch 432 to the collector of the transistor. Phantom capacitance due to the position of the other elements is produced as represented by capacitor 436 connected by dotted lines in parallel with the inductors 416 and 420.

When the switch 432 is closed, the transistor 408 is immediately turned on to conduct and produce several oscillations which continue until the capacitor 424 charges and turns off the transistor. The capacitor 424 then discharges through the base-collector electrodes of the transistor 408 which then causes the transistor to again turn on to produce oscillations. When a conducting path is established between the electrodes 208 and 212, the base and emitter electrodes of the transistor 408 are shorted to maintain the transistor in the "off" condition. The detector/transmitter 4 is then prevented from transmitting the oscillatory or pulse signals.

The amount of urine necessary to cause the disablement of the transistor 408 can be controlled by adjusting the variable resistor 404. That is, the higher the resistance of the variable resistor 404, the more urine is required to cause a shorting between the electrodes 208 and 212.

The thermistor 412 allows for measuring the temperature of the patient which information is transmitted to the repeater section 8 for display on the voltmeter 44. As the body heat of the patient increases, the resistance of the termistor 412 decreases and the frequency of generation of the pulses increases. As the body heat decreases, the resistance of the termistor 412 increases and the pulse frequency decreases. Thus, an increase in body temperature results in an increase in frequency of the pulses, and vice versa, and this information is converted by the frequency-to-voltage convertor 40 for display on the voltmeter 44.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A system for detecting and signalling the presence of urine in a diaper or similar article of clothing comprising
    detector/transmitter means attachable to the diaper for producing and transmitting a signal when no urine or other conductive matter is present in the diaper,
    receiver means for receiving the signal transmitted remotely by the detector/transmitter means for producing a received signal in response thereto,
    timer means for producing a time-out signal if no received signal is produced for a predetermined period of time,
    repeater means responsive to the time-out signal for transmitting a radio signal,
    second receiver means for receiving the radio signal and for producing an indicator signal, and
    indicator means for producing a visual and/or audible indication in response to production of the indicator signal.

2. A system as in claim 1 wherein said detector/transmitter means includes oscillator means for continuously transmitting a series of signal pulses when no urine or other conductive matter is present in the diaper.

3. A system as in claim 2 wherein said detector/transmitter means further includes a pair of electrodes disposed adjacent one another and coupled to the oscillator means such that when a conductive path is established between the electrodes, the oscillator means is disabled.

4. A system as in claim 3 wherein said electrodes comprise elongate conductor strips, said system further including a strip of material one side of which includes an adhesive, said conductor strips being carried on said one side of the strip of material generally in parallel with one another.

5. A system as in claim 4 wherein said detector/transmitter means further includes a housing having a generally planar profile in which is disposed the oscillator means, and a pair of electrical contact elements disposed on the exterior of the housing in a position to be contacted by respective electrodes carried by the strip of material.

6. A system as in claim 5 wherein said detector/transmitter means further includes attachment means supported by the housing for attaching the housing to the edge of a diaper or the like.

7. A system as in claim 3 further including a temperature detecting means joined to the detector/transmitter means for producing a signal representing the temperature of items contacted by the detector/transmitter means.

8. A system as in claim 7 wherein said temperature detecting means comprises a thermistor coupled to the oscillator to cause an increase in the frequency of oscillation of the oscillator as the temperature increases.

9. A system as in claim 8 further including a frequency-to-voltage converter coupled to the receiver means for producing a voltage signal whose magnitude is proportional to the frequency of pulses received by the receiver means, and voltage indicating means coupled to the frequency-to-voltage converter for producing a visual indication of the voltage output of the converter.

10. A system as in claim 9 wherein said oscillator means includes
    a battery,
    a transistor coupled by its collector to one side of the battery,
    a first inductor coil coupled between the emitter of the transistor and the other side of the battery, and
    a capacitor and second inductor coil connected in series between the base and emitter of the transistor,
    wherein one of said electrodes is coupled to the base of the transistor and the other of said electrodes is coupled to the emitter of the transistor.

11. A system as in claim 1 further comprising a plurality of detector/transmitter means, a plurality of receiver means each for producing a receive signal in response to receipt of a signal from a corresponding detector/transmitting means, a plurality of timer means each coupled to a respective receiver means for producing a time-out signal if no receive signal is produced for a predetermined period of time by the respective receiver means, and a plurality of repeater means coupled to a respective timer means for transmitting a radio signal when the respective timer means produces a time-out signal.

12. A system as in claim 11 wherein each of said repeater means includes
    an encoder means responsive to the respective time-out signal for producing a unique encoded radio signal identifying a respective detector/transmitter means and second transmitter means for transmitting the encoded radio signal, and wherein said indicator means includes decoder means for decoding each transmitted encoded radio signal to produce a decoded signal, and a plurality of indicator devices, each responsive to a different decoded signal for producing a visual signal identifying a respective detector/transmitter means.

13. A system as in claim 12 wherein said indictor means further includes patient identifying means positioned on or adjacent to each indictor device.

14. A system as in claim 13 wherein said indicator means further includes means for producing an audible signal for each transmitted encoded radio signal received by the second receiver means.

* * * * *